United States Patent [19]

Yoshikumi et al.

[11] Patent Number: 4,748,159

[45] Date of Patent: May 31, 1988

[54] METHOD FOR THE TREATMENT OF TUMORS

[75] Inventors: Chikao Yoshikumi, Tokyo; Yoshio Ohmura, Chiba; Fumio Hirose, Tokyo; Masanori Ikuzawa, Tokyo; Kenichi Matsunaga, Tokyo; Takayoshi Fujii, Tokyo; Minoru Ohhara, Tokyo; Takao Ando, Tokyo, all of Japan

[73] Assignee: Kureha Kagaku Kogyo Kabushiki Kaisha, Japan

[21] Appl. No.: 931,974

[22] Filed: Nov. 24, 1986

Related U.S. Application Data

[60] Continuation of Ser. No. 686,737, Dec. 27, 1984, abandoned, which is a division of Ser. No. 584,629, Feb. 29, 1984, Pat. No. 4,555,505, which is a continuation-in-part of Ser. No. 484,592, Apr. 13, 1983, Pat. No. 4,559,327, which is a continuation-in-part of Ser. No. 289,226, Aug. 3, 1981, abandoned, which is a division of Ser. No. 102,535, Dec. 11, 1979, Pat. No. 4,313,939, which is a continuation-in-part of Ser. No. 039,218, May 15, 1979, abandoned.

[30] Foreign Application Priority Data

May 26, 1978 [JP] Japan .................................. 53-63146
Dec. 29, 1978 [JP] Japan ................................ 53-161386
Dec. 29, 1979 [JP] Japan ................................ 53-161385

[51] Int. Cl.$^4$ .......................... A61K 31/70; C07H 1/00
[52] U.S. Cl. ......................................... 514/42; 536/22
[58] Field of Search ............................. 536/22; 514/42

[56] References Cited

U.S. PATENT DOCUMENTS

| | | | |
|---|---|---|---|
| 2,659,689 | 11/1953 | Schreiber | 536/18 |
| 3,655,884 | 4/1972 | Rossi et al. | 514/42 |
| 4,058,550 | 11/1977 | Shepard et al. | 536/715 |
| 4,311,694 | 1/1982 | Krueger et al. | 428/180 |
| 4,315,921 | 2/1982 | Yoshikumi et al. | 514/42 |
| 4,322,408 | 3/1982 | Yoshikumi et al. | 536/22 |
| 4,322,409 | 3/1982 | Yoshikumi et al. | 514/42 |
| 4,380,536 | 4/1983 | Yoshikumi et al. | 536/22 |
| 4,431,939 | 2/1982 | Yoshikumi et al. | 514/23 |

OTHER PUBLICATIONS

Chem. Abst. 92:94677a, 1980.
Bondonna et al., Combination Chemotherapy as an Adjuvant Treatment in Operable Breast Cancer, New England Journal of Medicine, vol. 294, pp. 405–410.
Fisher et al., 1–Phenylalanine Mustard (L–PAM) in the Management of Primary Breast Cancer, New England Journal of Medicine, vol. 292, pp. 117–122.
Chem. Abstracts, vol. 92 (1980) p. 94677(a).
Chem. Abstracts, vol. 69, No. 1 (1968) p. 1022, 106287.
Chem. Abstracts, vol. 48: 2001–2003.
Johnson, et al., "Cancer Treatment Reviews", 1975, vol. 2, pp. 1–6.

Primary Examiner—J. R. Brown
Assistant Examiner—John W. Rollins, Jr.
Attorney, Agent, or Firm—Wegner & Bretschneider

[57] ABSTRACT

Disclosed is a method for the treatment of hyperglycemia, hyperlipemia, inflammatory diseases, pains due to the accentuation of central nerve, pyrexia due to the accentuation of central nerve or tumor, which comprises administering to a patient suffering therefrom a pharmaceutically effective amount of p-aminobenzoic acid-N-L-rhamnoside or a pharmaceutically acceptable salt thereof.

14 Claims, 2 Drawing Sheets

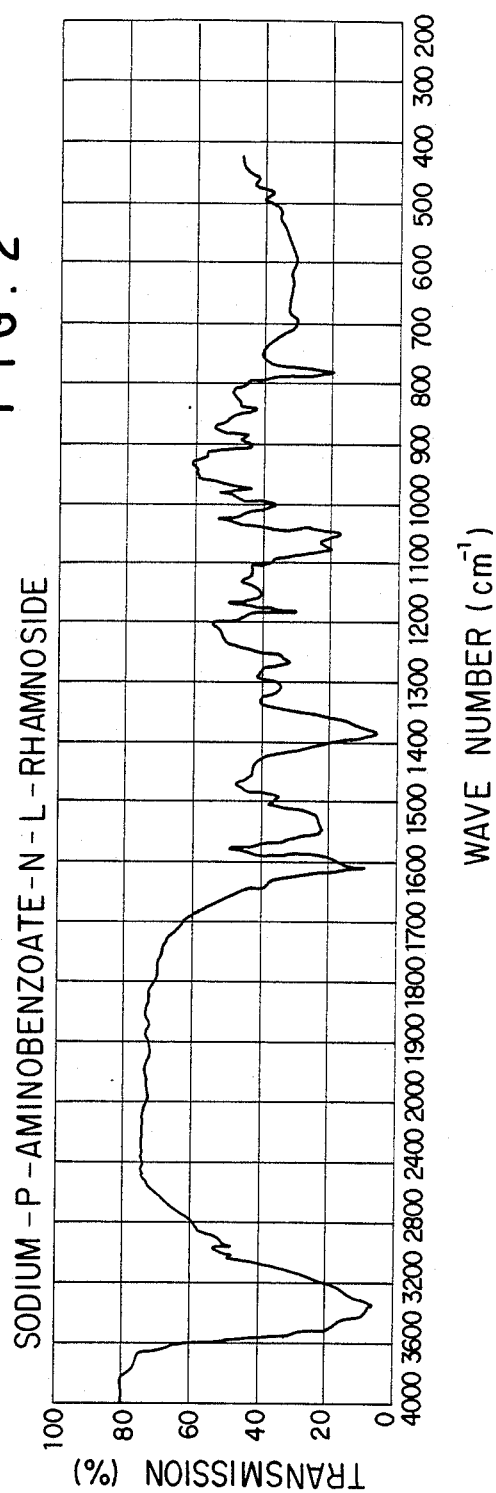

METHOD FOR THE TREATMENT OF TUMORS

CROSS-REFERENCES TO RELATED APPLICATION

This application is a continuation of U.S. application Ser. No. 686,737, filed Dec. 27, 1984, now abandoned, which is a division of application Ser. No. 584,629 filed Feb. 29, 1984, now U.S. Pat. No. 4,555,505, which is a continuation-in-part of application Ser. No. 484,592 filed Apr. 13, 1983, now U.S. Pat. No. 4,559,327, which is a continuation-in-part of application Ser. No. 289,226 filed Aug. 3, 1981, now abandoned, which is a division of application Ser. No. 102,535 filed Dec. 11, 1979, now U.S. Pat. No. 4,313,939, which is a continuation-in-part of application Ser. No. 39,218 filed May 15, 1979, now abandoned.

BACKGROUND OF THE INVENTION

The present invention relates to a method of inhibiting tumor growth in a patient suffering therefrom and a method for the treatment of hyperglycemia, hyperlipemia, inflammatory diseases, pains due to the accentuation of central nerve, pyrexia due to the accentuation of central nerve or tumor, which comprises administering to a patient suffering therefrom a pharmaceutically effective amount of p-aminobenzoic acid-N-L-rhamnoside or a pharmaceutically acceptable salt thereof.

The inventors of the present invention, during the course of searching chemical compounds having antitumor activity, have found that the above-mentioned chemical compound has a number of physiological activities such as blood sugar-reducing acitivity, antihypertensive activity, blood lipid-reducing activity, antiinflammatory activity and central nerve-depressing activity in addition to its antitumor activity.

Although the above-mentioned aminobenzoic acid deriyatives are known compounds, no report has been found on the physiological activity of the compounds.

"Inoue, et al. N-Glycosides. XIX. Preparation of anthranilic acid N-glycosides., Chemical Abstracts, Vol. 48 (1954), Column 2001 i." and "Inoue, et al. N-Glycosides. XXV. Paper chromatography of N-glycosides., Chemical Abstracts, Vol 48 (1954), Column 2003 a." disclose the chemical syntheses of the compounds which are the active ingredients of the pharmaceutical composition of the present invention. However, there is no utility disclosed in these prior arts and no teaching of pharmaceutical "dosage unit forms".

Furthermore, although U.S. Pat. No. 2,659,689 discloses a p-aldimino benzoic ester and a composition for protecting the human skin from erythema producing rale, the composition comprising a solution of p-aldimino benzoic ester, there is no teaching of pharmaceutical "dosage unit forms".

SUMMARY OF THE INVENTION

In a first aspect of the present invention, there is provided a method of inhibiting tumor growth in a patient suffering therefrom which comprises administering to said patient a pharmaceutically effective, amount of p-aminobenzoic acid-N-L-rhamnoside or a pharmaceutically acceptable salt thereof.

In a second aspect of the present invention, there is provided a method for the treatment of hyperglycemia, which comprises administering to a patient suffering therefrom a pharmaceutically effective amount of p-aminobenzoic acid-N-Lrhamnoside or a pharmaceutically acceptable salt thereof.

In a third aspect of the present invention, there is provided a method for the treatment of hyperlipemia, which comprises administering to a patient suffering therefrom a pharmaceutically effective amount of p-aminobenzoic acid-N-Lrhamnoside or a pharmaceutically acceptable salt thereof.

In a fourth aspect of the present invention, there is provided a method for the treatment of inflammatory diseases, which comprises administering to a patient suffering therefrom a pharmaceutically effective amount of p-aminobenzoic acid-N-L-rhamnoside or a pharmaceutically acceptable salt thereof.

In a fifth aspect of the present invention, there is provided a method for the treatment of pains due to the accentuation of central nerve, which comprises administering to a patient suffering therefrom a pharmaceutically effective amount of p-aminobenzoic acid-N-L-rhamnoside or a pharmaceutically acceptable salt thereof.

In a sixth aspect of the present invention, there is provided a method for the treatment of pyrexia due to the accentuation of central nerve, which comprises administering to a patient suffering therefrom a pharmaceutically effective amount of p-aminobenzoic acid-N-L-rhamnoside or a pharmaceutically acceptable salt thereof.

In a seventh aspect of the present invention, there is provided a method for the treatment of tumor, which comprises administering to a patient suffering therefrom a pharmaceutically effective amount of p-aminobenzoic acid-N-L-rhamnoside or a pharmaceutically acceptable salt thereof.

BRIEF DESCRIPTION OF THE DRAWING

The annexed FIGS. 1 to 2 show respectively the infrared absorption spectra of respective compound No. 1 to No. 2 in Table 1.

DETAILED DESCRIPTION OF THE INVENTION

Figure 1:
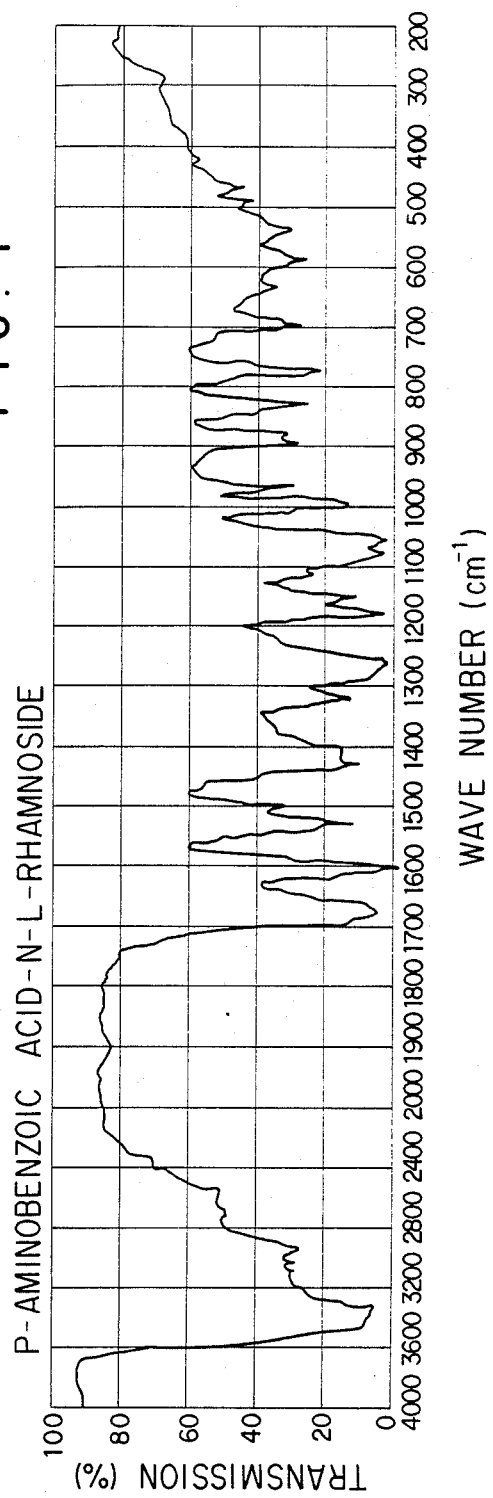

The active ingredient of the pharmaceutical composition of the present invention is a compound represented by the following formula:

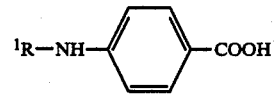

wherein $^1R$ denotes the residual group formed by removing the OH at 1(alpha) or 1 (beta) position from rhamnose, or its pharmaceutically acceptable salt selected from the group consisting of its Na, K, Mg, Ca and Al salts. The sugar moiety of the active ingredient has a structure of a pyranose ring.

The method of preparation of the active ingredient of the present invention is illustrated as follows:

A mixture of 4.5 to 5 g of p-aminobenzoic acid, 5–6 g of L-rhamnose and 0.1 to 0.5 g of ammonium chloride was heated in 40 to 90 ml of 95 to 100% ethanol or pure methanol under a reflux condenser to induce condensation. After the reaction is over, the reactant is left at room temperature or in a cool place and the crystals separated out are collected by filtering the reactant solution. These crystals are washed with water, ethanol or ethyl ether, and then recrystallized from an aqueous solution of methanol or ethanol.

In order to substitute the hydrogen atom of the carboxyl group of the thus prepared compound with a base, it is preferable to follow the known method. The compound, paraaminobenzoic acid-N-L-rhamnoside, is dissolved in an aqueous ethanolic solution and an inorganic salt is added to the solution to effect the substitution.

The physical properties of the compounds (the active ingredient of the pharmaceutical composition of the present invention) prepared by the above-mentioned methods are shown in Table 1, and their infrared absorption spectra are respectively shown in FIGS. 1 to 2. Methods of determination of the physical properties are as follows.

noside is qualified to be highly safe active ingredient of the pharmaceutical composition, having $LD_{50}$ more than 10 g/kg, regardless of the route of administration.

TABLE 2

| | Acute toxicity of the active ingredient | |
|---|---|---|
| | $LD_{50}$ in g/kg Route of administration | |
| Compound | Intraperitoneal | Oral |
| Sodium p-aminobenzoate-N—L-rhamnoside | 15.00 | 12.80 |

(2) Anti-microbial activity

Sodium p-aminobenzoate-N-L-rhamnoside was dis-

TABLE 1

| | Physical properties of the active ingredients | | | |
|---|---|---|---|---|
| Compound | Melting point (°C.) | Specific rotation $[\alpha]_D^{20}$ | Elementary analysis (%) C:H:N | Ultraviolet absorption Maximum (millimicron) |
| 1. p-aminobenzoic acid-N—L-rhamnoside | 169-170 (decomp.) | −28.6 in 94% ethanol | 55.0:6.2:4.8 (55.1:6.0:4.9) | 290, 220 |
| 2. Sodium p-aminobenzoate-N—L-rhamnoside | 173-178 (decomp.) | +80 in water | 51.0:5.1:4.8 (51.1:5.2:4.6) | 273 |

Note:
( :: ) = theoretical values of C, H and N (%).

(1) Melting point: determined by the use of micro melting point determination apparatus made by Yanagimoto Works, Japan.

(2) Specific rotation: determined by using direct-reading polarimeter.Model OR-50 made by Yanagimoto Works, Japan, with a thickness of 50 mm of an aqueous ethanolic solution of the acidic active ingredient and an aqueous solution of the sodium salt of the acidic active ingredient.

(3) Molecular composition: Elementary analysis was carried out by using CHN-Coder Model MT-2 made by Yanagimoto Works, Japan.

(4) Ultraviolet absorption spectrum: by using self-recording spectrophotometer Model PS-3T made by Hitachi Works, Japan, on an aqueous ethanolic solution of the acidic active ingredient and of an aqueous solution of the sodium salt of the acidic active ingredient.

(5) Infrared absorption spectrum: determined by KBr-method using infrared absorption spectrometer Model DS-701G made by Nippon Bunko Co., Ltd., Japan. The chart number of the spectrogram coincides with the number of specimens of the active ingredient The followings are the physiological properties of the active ingredient of the pharmaceutical composition of the present invention described in the order of (1) acute toxicity, (2) antimicrobial activity, (3) mutagenicity, (4) delayed-type intracutaneous reaction and (5) antibody-producing activity (1) Acute toxicity Acute toxicity of sodium p-aminobenzoate-N-L-rhamnoside was examined by respective intraperitoneal and oral (forcible) administration to ICR-JCL mice. The specimen was dissolved in the physiological saline solution in intraperitoneal administration, and dissolved in distilled water in oral administration.

Their symptoms were observed after administration until the 7th day of administration, and $LD_{50}$ of the specimen was obtained from the mortality accumulated to the 7th day, according to the graphic method of Litchfield-Wilcoxon. The result is shown in Table 2. As is seen in Table 2, sodium p-aminobenzoate-N-L-rhamsolved in distilled water at a series of two fold dilution system. These diluted solutions were mixed with agar medium in 9 times by volume and the mixture was poured into a petridish. Heart infusion agar medium was used for bacteria, and Sabouraud's agar medium was used for fungi. After streaking with the preculture, the inoculated plates were incubated at 37° C. for 20 to 24 hours for bacteria and at 25° C. for 3 to 7 days for fungi, and then the growth was examined. The following microorganisms were used for assessing the antimicrobial activity:

*Pseudomonas aeruginosa* IAM 1514
*Escherchia coli* IFO 12734
*Staphylococcus aureus* 209 P
*Bacillus subtilis* IAM 1069
*Saccharomyces cerevisiae* IAM 4207
*Candida albicans* ATCC 752
*Trichophyton mentagrophytes* IFO 6124
*Aspergillus niger* IAM 3001

As the result of the above-mentioned tests, it was found that sodium p-aminobenzoate-N-L-rhamnoside did not show any growth inhibition against all the microorganisms, at a concentration of 1 mg/ml.

(3) Mutagenicity

As the first stage, sodium p-aminobenzoate-N-L-rhamnoside was tested by rec-assay (i), and as the second stage, it was tested by reversion assay (ii).

(i) A strain of *Bacillus subtilis* M 45, a defectant of recombination repair, and a wild strain of *Bacillus subtilis* H 17 keeping recombination repair activity were inoculated to make their own streaks not crossed at the start on a B-2 agar culture plate (made by dissolving 10 g of meat extract, 10 g of polypeptone, 5 g of sodium chloride and 15 g of agar in 1000 ml of distilled water at a pH of 7.0). Then, a circular sheet of filter paper 8 mm in diameter, which absorbed 0.04 ml of an aqueous solution of sodium p-aminobenzoate-N-L-rhamnoside (using sterilized water) was put on the surface of the agar plate so as to cover the starting point of the abovementioned streaks of bacterial culture. The inoculated B-2 agar culture was kept at 37° C. for a night and the length of growth-inhibited region was measured. Kanamycin was used as the negative control and Mitomycin C was used as the positive control. The results of the rec-assay are shown in Table 3.

(ii) The strains TA 98 and TA 100 (both are histidine requiring) of *Salmonella typhimurium* were used in the reversion assay.

Into 2 ml of a soft agar culture medium (the medium itself contains 6 g of sodium chloride and 6 g of agar in 1000 ml of distilled water) to which one tenth by volume of an aqueous solution of 0.5 mM of biotin and 0.5 mM of histidine had been added, 0.1 ml of the bacterial suspension and 0.1 ml of an aqueous solution of sodium p-aminobenzoate-N-L-rhamnoside were admixed and the mixture was layered on the minimum agar culture medium. After 2 days of incubation at 37° C., the number of revertant colonies was counted. Furylfuramide (AF-2) was used as the positive control. The results of the reversion assay are shown in Table 4.

As is seen in Table 3, sodium p-aminobenzoate-N-L-rhamnoside did not show any mutagenicity at a high concentration of 5000 microgram/disk. And as is seen in Table 4, the rate of occurrence of mutation by the active ingredient of the pharmaceutical composition of the present invention did not show any difference from that in the control to which no substance was added, even at a high concentration of 5000 microgram/plate. These findings demonstrate that the active ingredient is safe in view of mutagenicity.

TABLE 3

| | Result of rec-assay | | | |
|---|---|---|---|---|
| | Concentration | Length of growth-inhibition zone | | Difference* |
| Compound | (μg/disk) | H 45 (mm) | H 17 (mm) | (mm) |
| Sodium p-aminobenzoate-N—L-rhamnoside | 500 | 0 | 0 | 0 |
| | 5,000 | 0 | 0 | 0 |
| Kanamycin | 10 | 5 | 4 | 1 |
| Mitomycin C | 0.05 | 12 | 2 | 10 |

Note:
*Difference = length of inhibition zone of M 45 minus length of inhibition zone of H 17.

TABLE 4

| | Result of reversion assay | | |
|---|---|---|---|
| | Concentration | Number of revertant colonies (n/plate) | |
| Compound | (μg/plate) | TA 100 | TA 98 |
| Sodium p-aminobenzoate-N—L-rhamnoside | 5,000 | 73 | 4 |
| Furylfuramide | 0.1 | 911 | 167 |
| Control (nothing added) | — | 149 | 13 |

(4) Delayed-type intracutaneous reaction

In order to know the effects of the active ingredient on cellular immunity, the foot pad reaction test was carried out using ICR-JCL mice as experimental animals and erythrocytes of sheep as an antigen.

A mouse was primary-sensitized by injecting 0.2 ml of 10% suspension of sheep erythrocytes in physiological saline solution from the caudal vein and after 7 days of the first sensitization, 0.05 ml of 40% suspension of sheep erythrocytes in physiological saline solution was injected in the foot pad for the second sensitization. The thickness of the foot pad was determined on the next day. The administration of the active ingredient of the pharmaceutical composition of the present invention was carried out at the dosage of 250 mg/kg/day once a day for consecutive 5 days centering around the day when the first sensitization was carried out.

As the result, the increment of the thickness of the foot pad of the mouse administered with the active ingredient showed no significant difference as compared to the increment in the group of mouse not administered with the active ingredient.

(5) Antibody-producing activity

In order to know the effects of the active ingredient on humoral immunity, the hemagglutination test was carried out using ICR-JCL mice sensitized with sheep erythrocytes.

A mouse was sensitized by injecting 0.2 ml of 10% suspension of sheep erythrocytes in physiological saline solution from the caudal vein and after 7 days of sensitization the mouse blood was sampled for the hemagglutination test of determination of the autibody-producing activity. The active ingredient was administered for consecutive 5 days centering around the day of sensitization, intraperitoneally at the dosage of 250 mg/kg/day.

As the result, there was no significant difference in agglutination titer between the group administered with the active ingredient and the control group.

In the case where the pharmaceutical composition is used as an antiinflammatory agent, it is able to use the pharmaceutical composition in the form which is convenient to obtain the effectiveness according to the kinds and the symptoms of the disease, and moreover, the active ingredient may be used as itself or may be used as mixtures combined with any diluent allowable in pharmaceutical process and with other medicines.

The pharmaceutical composition of the present invention is administered orally or parenterally and accordingly, the pharmaceutical composition of the present invention may take any form optionally for the oral or parenteral administration.

The pharmaceutical composition of the present invention may be offered as a form of unit administration. The form of the pharmaceutical composition of the present invention may be powder, granule, tablet, sugar-coated tablet, capsulated one, suppository, suspension, solution, emulsifiable concentrate, ampouled one, injection, etc. As a diluent, any one of solids, liquids and semisolids may be utilized, for instance, excipients, fillers, binders, wetting agents, disintegrating agents, surfactants, demulcents, dispersing agents, buffering agents, perfumes, preservatives, dissolution aids and solvents. Moreover, one or more than one of these adjuvants may be used in combination or in mixtures.

The pharmaceutical composition of the present invention may be formulated by any known method, and the amount of the active ingredient contained in the composition (preparation) is generally from 0.01% to 100% by weight.

The pharmaceutical composition of the present invention may be administered orally or parenterally to human or animals, however, it is preferably administered orally. Sublingual administration is included in oral administration. Parenteral administration includes subcutaneous injection, intramuscular injection and intravenous injection and the injection by drop method.

The dose of the pharmaceutical composition of the present invention depends upon the age, the personal difference and the state of disease, and whether the object is human or animal and accordingly, an extraordinal amount may be administered than the following dose: Generally, for human, the oral dose is 0.1–1000 mg/kg body weight/day, preferably 1–500 mg/kg/day and the parenteral dose is 0.01–200 mg/kg/day, preferably 0.1–100 mg/kg/day divided into 1–4 parts, one part being administered in one time.

The present invention will be more precisely explained while referring to Examples as follows.

However, the present invention is not restricted to Examples under mentioned. From the foregoing description, one skilled in the art can easily ascertain the essential characteristics of the present invention, and without departing from the spirit and scope thereof, can make various changes and modifications of the invention to adapt it to various usages and conditions.

EXAMPLE 1

(Production of p-aminobenzoic acid-N-L-rhamnoside and its sodium salt)

A mixture of 3 g of p-aminobenzoic acid, 4 g of L-rhamnose and 0.1 g of ammonium chloride was heated in 30 ml of 94% ethanol under a reflux condenser. After the reaction was over, crystals separated out when the reaction mixture was left at room temperature. The crystals thus obtained by filtering were washed with water and an aqueous methanolic solution, and then recrystallized from 50% methanol. The recrystallized crystals were colorless needles. Yield was 30.9%.

Thus obtained p-aminobenzoic acid-N-L-rhamnoside was dissolved gradually into an aqueous 1% sodium hydroxide solution containing in total the calculated amount of sodium hydroxide and after filtering, the solution was condensed under reduced pressure. The crystals which separated out by the addition of a large excess of acetone to the condensate was dehydrated and dried. Colorless crystal of sodium salt was obtained at the yield of 100% based on the p-aminobenzoic acid-N-L-rhamnoside and at the total yield of 30.9%.

EXAMPLE 2

(Formulation)

10 parts by weight of sodium p-aminobenzoate-N-L-rhamnoside, 15 parts by weight of (heavy) magnesium oxide and 75 parts by weight of lactose were uniformly mixed and formulated into powder or granules. The power is filled in capsules to be capsulated formulation.

EXAMPLE 3

(Formulation)

45 parts by weight of sodium p-aminobenzoate-N-L-rhamnoside, 15 parts by weight of starch, 16 parts by weight of lactose, 21 parts by weight of crystalline cellulose, 3 parts by weight of polyvinyl alcohol and 30 parts by weight of water were uniformly mixed, crushed and formulated, and then dried and shifted to be granules.

EXAMPLE 4

(Formulation)

Granules were prepared as in Example 3, and the mixture of 96 parts by weight of this granule and 4 parts by weight of calcium stearate was compression-formulated to be tablets 10 mm in diameter.

EXAMPLE 5

(Formulation) 94 parts by weight of sodium p-aminobenzoate-N-L-rhamnoside, 6 parts by weight of polyvinyl alcohol and 30 parts by weight of water were mixed and the mixture was processed as in Example 3 to be granules. To 90 parts by weight of the thus processed granules 10 parts by weight of crystalline cellulose were mixed and the mixture was compressionformulated to be tablets 8 mm in diameter. The tablets were coated with syrup, gelatine and precipitated calcium carbonate to be coated tablets.

EXAMPLE 6

(Formulation)

0.6 part by weight of sodium p-aminobenzoate-N-L-rhamnoside, 2.4 parts by weight of a non-ionic surfactant and 97 parts by weight of physiological saline solution were mixed under heating and then the mixture was sterilized to be an injection.

EXAMPLE 7

The followings are the pharmacological properties of the active ingredient of the pharmaceutical composition of the present invention described in the order of (1) blood sugarreducing activity, (2) antihypertensive activity, (3) anti-tumour activity, (4) analgetic activity, (5) antipyretic activity, (6) antiinflammatory activity and (7) blood lipid reducing activity.

(1) Blood sugar-reducing activity

Streptozotocin was administered intraperitoneally to a group of Wistar rats at a dosage of 60 mg/kg and after confirming the positivity of urinary sugar of the animals on the 8th day, regular insulin was further administered to the rats to reduce both the urinary sugar and the blood sugar. Out of thus treated animals, those which certainly showed a higher urinary sugar value and also a higher blood sugar value after a few days of insulin-administration were used as the model animals suffering from artificial diabetes mellitus. Sodium p-aminobenzoate-N-L-rhamnoside was administered to the model animals orally as a solution in distilled water at the respective dosages of 30 and 300 mg/kg. Blood specimens were collected after 3 and 6 hours of the administration, and the determination of glucose in the specimen was carried out by using a RaBA-kit (made by Chugai Pharmaceutical Co., Japan) according to the enzyme method.

The results are shown in Table 5. As is seen in Table 5, the difference between the values of blood sugar before and after the administration of the active ingredient (Δ value) was conspicuously larger than Δ value of control.

TABLE 5

| | Blood sugar-reducing activity | | |
|---|---|---|---|
| | | Change (Δ value) (mg/dl) of blood sugar after | |
| Compound | Dose (mg/kg) | 3 hrs. | 6 hrs. |
| Sodium p-aminobenzoate- | 30 | −157 | −151 |
| N—L-rhamnoside | 300 | −115 | −121 |
| Control | — | −36 | −39 |

(2) Antihypertensive activity

An aqueous solution of sodium p-aminobenzoate-N-L-rhamnoside in distilled water was orally administered to rats of spontaneous hypertension at respective dosages of 30 and 300 mg/kg and their blood pressure was determined after 3 and 6 hours of administration by a sphygmomanometer (made by Ueda Works, Japan, Model USM-105R). The difference of blood pressures before and after the administration was used to evaluate the antihypertensive activity of sodium p-aminobenzoate-N-L-rhamnoside. Mean value of blood pressure of the abovementioned rats in spontaneous hypertension was 200 mmHg.

The results are shown in Table 6. As is seen in Table 6, sodium p-aminobenzoate-N-L-rhamnoside clearly showed the antihypertensive effect.

TABLE 6

| | Antihypertensive activity | | |
|---|---|---|---|
| | | Reduced amount of blood pressure after | |
| Compound | Dose rate (mg/kg) | 3 hrs. (mmHg) | 6 hrs. |
| Sodium p-aminobenzoate-N—L-rhamnoside | 30 | 14 | 14 |
| | 300 | 20 | 25 |
| Control | — | −2* | 2 |

Note:
*Blood pressure raised by 2 mmHg.

(3) Antitumour activity (against transplanted tumour cells)

(3-1) Against Sarcoma-180

Sarcoma-180 were transplanted subcutaneously into the right axilla of ICR-JCL mice at the rate of $1 \times 10^6$ cells/mouse, and from after 24 hours of transplantation an aqueous solution of sodium p-aminobenzoate-N-L-rhamnoside in sterilized physiological saline solution was orally and forcibly administered every other day at a dose rate of 500 mg/kg, 10 times in all. On the 25th day of the transplantation, the nodular tumour(s) was extirpated and weighed.

The inhibition ratio (I.R.) (%) of the active ingredient was calculated by the following formula:

$$(1 - T/C) \times 100 = I.R. (\%)$$

wherein T: mean weight of the tumour(s) in treated group of mice and C: mean weight of the tumour(s) in control group* of mice.
Note: * Mice transplanted, but not administered.

The result of the test is shown in Table 7. As is seen in Table 7, sodium p-aminobenzoate-N-L-rhamnoside exhibited a considerably high antitumour acitivity.

(3-2) Against Melanoma B-16

A small slice (3 mm in square) of Melanoma B-16 which had been maintained by transplantation in generations subcutaneous ly in C57BL/6 mice was transplanted subcutaneously into the axilla of each of female BDF mice of 5 weeks after birth (10 animals/group). The specimen, sodium p-aminobenzoate-N-L-rhamnoside, was orally and forcibly administered daily, in total 10 times, from after 24 hours of the transplantation at a rate of 100 or 500 mg/kg after dissolving into an aqueous physiological saline solution. By observing the mortality of the thus transplanted mice for 60 days after transplantation, the rate of elongation of their lives was obtained from the mean survival days and is shown also in Table 7.

(3-3) Against Breast cancer MM-102

Breast cancer MM-102 which had been maintained by transplantation in generations intraperitoneally in C3H/Hc mice and taken from the mouse of the 7th generation was intraperitoneally transplanted to each of the female mice of the same strain 5 weeks after birth at a rate of $1 \times 10^6$ cells/animal (10 animals per group).

The specimen, sodium p-aminobenzoate-N-L-rhamnoside, was orally and forcibly administered daily, in total 10 times, from after 24 hours of transplantation at a dose rate of 100 or 500 mg/kg after dissolving into an aqueous physiological saline solution By observing the mortality of the thus transplanted mice for 60 days after transplantation, the rate of elongation of their lives was obtained from the mean survival days, and shown also in Table 7.

(3-4) Against Liver Cancer MH-134

Liver cancer MH-134 which had been maintained by transplantation in generations intraperitoneally in female C3H/Hc mice and taken from the mouse of the 7th generation was intraperitoneally transplanted to each of the female C3H/Hc mice of 5 weeks after birth at a rate of $1 \times 10^6$ cells/animal (10 animals per group). The specimen, sodium p-aminobenzoate-N-L-rhamnoside, was orally and forcibly administered daily, in total 10 times, at 100 or 500 mg/kg after dissolving in an aqueous physiological saline solution to the thus transplanted mice.

By observing the mortality of the thus treated mice for 60 days after transplantation, the rate of elongation of their lives was obtained from the mean survival days and shown also in Table 7.

TABLE 7

| Antitumour Activity against Transplanted Tumour Specimen: Sodium p-aminobenzoate-N—L-rhamnose | | | | | |
|---|---|---|---|---|---|
| Tumour | Animal | Route of Administration | Amount of administration (mg/kg) × 10 | Mean survival days | ILS (%) |
| Sarcoma-180 | LCR-JCL mouse | oral | 500 | — | 72.5 (I.R.)* |
| Malanoma-B-16 | BDF₁ mouse | oral | 100 | 25.6 | 132.0 |
| | | | 500 | 26.2 | 135.1 |
| | | | 0 (control) | 19.4 | — |
| Breast cancer MM-102 | C3H/Hc mouse | oral | 100 | 21.0 | 129.6 |
| | | | 500 | 22.3 | 137.7 |
| | | | 0 (control) | 16.2 | — |
| Liver cancer | C3H/Hc mouse | oral | 100 | 21.7 | 140.3 |
| | | | 500 | 21.9 | 141.3 |

TABLE 7-continued

Antitumour Activity against Transplanted Tumour
Specimen: Sodium p-aminobenzoate-N—L-rhamnose

| Tumour | Animal | Route of Administration | Amount of administration (mg/kg) × 10 | Mean survival days | ILS (%) |
|---|---|---|---|---|---|
| | | | 0 (control) | 15.5 | — |

Note:
Against Sarcoma-180 only the index of tumour growth inhibition was tested.

(4) Analgetic activity

Determination by the mechanical stimulation method (by applying pressure)

Female ICR mice which showed a threshold value of pain of 50 to 80 mmHg when their tail base part was pressured by a pressure stimulation apparatus (made by Natsume Works, Japan) of Takagi and Kameyama were chosen at test animals, ten animals comprising a group.

After administering sodium p-aminobenzoate-N-L-rhamnoside, the test was carried out as the time passes and the applied pressure and the time period until the animal showed a quasi-escaping reaction were determined to evaluate the analgetic activity of the active ingredient.

The result is shown in Table 8. As is seen in Table 8, the pressure applied on animals when the animal showed the quasi-escaping reaction was higher in animals to which sodium p-aminobenzoate-N-L-rhamnoside had been applied than in animals not administered, and the time period from the beginning to the time point when the animal showed the reaction was longer in animals administered with the active ingredient than in animals not administered. Thus, the analgetic activity of sodium p-aminobenzoate-N-L-rhamnoside was confirmed.

Determination by the chemical stimulation method

Sodium p-aminobenzoate-N-L-rhamnoside was orally administered to a group (ten animals) of female ICR mice of age of 5 to 6 weeks, and after 30 min of the administration an aqueous 0.6% acetic acid solution was intraperitoneally injected into the mouse at a dose rate of 0.1 ml/10 g of body weight. The number of writhing syndrome which occurred in the mouse during 10 minutes after 10 minutes of intraperitoneal administration was recorded The analgetic activity was evaluated from the writhing syndrome inhibiting ratio obtained by the following formula:

$(1-T/C) \times 100 = $ writhing syndrome—inhibiting ratio (%)

wherein
T: mean number of writhing syndrome in the group administered.
C: mean number of writhing syndrome in the control group.

The result is shown in Table 9. As is seen in Table 9, the active ingredient of the pharmaceutical composition of the present invention showed analgetic activity. The abovementioned process was carried out following the method of Kostet et al. (1959).

TABLE 8

Analgetic activity by the mechanical stimulation method

| Compound | Quasi-escape reaction pressure at time until | |
|---|---|---|
| | (mmHg) occurrence | (sec) |
| Sodium p-aminobenzoate-N—L-rhamnoside | 92 | 42 |
| Control | 70 | 33 |

Note:
Amount of administration, 1000 mg/kg p.o.

TABLE 9

Analgetic activity by the chemical stimulation method

| Compound | I.R. (%) |
|---|---|
| Sodium p-aminobenzoate-N—L-rhamnoside | 75.0 |

Note:
Amount of administration was 1000 mg/kg p.o.

Antipyretic activity Following the method of Winter et al. (1961), a 20% suspension of beer yeast was subcutaneously injected to a group (consisting of 6 animals) of rats, and after 10 hours of fasting, sodium p-aminobenzoate-N-L-rhamnoside was orally administered to the rats and their rectal temperature was determined The antipyretic activity is expressed by the ratio of inhibiting pyrexia due to beer yeast (I.R. %) at the time when the antipyretic activity of the active ingredient is at its maximum according to the following formula:

$$\text{Antipyretic activity} = I.R. \ (\%) = \frac{C_1 - T}{C_1 - C_2} \times 100$$

wherein
T: mean rectal temperature of rats to which the active ingredient was administered.
$C_1$: mean rectal temperature of rats injected beer yeast, without the active ingredient.
$C_2$: mean rectal temperature of untreated rats (control).

The result is shown in Table 10. As is seen in Table 10, sodium p-aminobenzoate-N-L-rhamnoside exhibited a considerable antipyretic activity.

TABLE 10

Antipyretic activity

| Compound | Antipyretic activity (suppressing pyrexia) I.R. (%) |
|---|---|
| Sodium p-aminobenzoate-N—L-rhamnoside | 91.4 |

(6) Antiinflammatory activity (a) Carrageenin-edema inhibitory activity

Following the method of Van Arman et al. (1963), sodium p-aminobenzoate-N-L-rhamnoside was forcibly and orally administered to each rat of a group consisting of 10 animals at the dose rate of 1000 mg/kg, and after one hour of the administration 0.1 ml of 1% suspension of carrageenin in physiological saline solution was injected to their right foot pad. The volume of the foot pad was determined as time passes and the antiinflammatory activity was expressed by the ratio of inhibition of the swelling of the foot pad due to carrageenin by the active ingredient, using the determined value of 1–4 hours from the injection and calculating by the following formula:

$$(1 - T/C) \times 100 = I.R. \ (\%) = \text{antiinflammatory activity}$$

wherein
T: mean value of volumes of foot pad in administered animals.
C: mean value of volume of foot pad of control (not administered and then injected).

The result is shown in Table 11. As is seen in Table 11, the ingredient showed the inhibitory activity against the edema caused by catrageenin.

(b) Antigranuloma activity

Following the method of Winter et al. (1963), two cotton wool pellets were implanted into the skin of back of each rat of a group consisting of 6 rats at the symmetrical positions having the median line as the axis of symmetry, the weight of one. pellet being 30±1 mg. Oral administration of 1000 mg/kg/day of sodium p-aminobenzoate-N-L-rhamnoside was carried out for consecutive 7 days. On the 8th day, the granuloma formed in the rats was extirpated and weighed after drying. The antigranuloma activity expressed by the ratio of inhibition of the growth of the granuloma (I.R., %) was calculated in a manner as shown in (6) (a), and the result is shown in Table 11. As is seen in Table 11, sodium p-aminobenzoate-N-L-rhamnoside exhibited the inhibiting activity of growth of the granuloma.

(c) Antiexudation activity

Following the method of Baris et al. (1965), a volume of air was injected subcutaneously in the back of each rat of a group consisting of 6 rats to make an air pouch, and then 0.5 ml of 1% cotton oil solution in sesame oil was injected into the pouch. The oral administration of 1000 mg/kg/day of sodium p-aminobenzoate-N-L-rhamnoside was then begun to continue for 5 days. On the 6th day, the amount of exudated liquid into the pouch was determined and the antiexudation activity expressed by the ratio of inhibitory activity to exudation was calculated in a manner as shown in (6) (a). The result is shown in Table 11. As is seen in Table 11, sodium p-aminobenzoate-N-L-rhamnoside exhibited the antiexudation activity.

(d) Antiadjuvant arthritis activity

Following the method of Fujiwara et al. (1971), Mycobacterium tuberculosis suspended in liquid paraffin was injected subcutaneously into the right foot pad of each rat of group consisting of 6 rats. After 14 days of the injection, rats with similar volume of the foot pad were chosen to form groups (10 animals/group), sodium p-aminobenzoate-N-Lrhamnoside was orally administered daily from the 15th day for consecutive 7 days. The volume of the foot pad of rats was determined, and the antiadjuvant arthritis activity of the active ingredient was calculated as the ratio of inhibiting the swelling of the foot pad by using the formula shown in (6) (a). The result is shown in Table 11. As is seen in Table. 11, sodium p-aminobenzoate-N-L-rhamnoside exhibited the antiadjuvant arthritis activity.

TABLE 11

| | Antiinflammatory activity | | | |
|---|---|---|---|---|
| Compound | Edema | Granuloma | Exudation | Arthritis |
| Sodium p-aminobenzoate-N—L-rhamnoside | 21.7 | 22.1 | 16.2 | 35.9 |

Note:
Amount of administration of sodium p-aminobenzoate-N—L-rhamnoside = 1000 mg/kg.

(7) Blood lipid reducing activity

Japanese male white rabbits were fed for about 3 months with solid feed (CR-1) containing 1% of cholesterol and those animals in which the increase of seral lipid component was confirmed were used as the model animals having experimental arteriosclerosis.

An aqueous solution of sodium p-aminobenzoate-N-L-rhamnoside in distilled water was administered respectively at the dose rates of 30 and 300 mg/kg orally and after the administration, blood specimen was collected as time passes from the auricular vein and the change of total cholesterol (determined by the enzyme method), phospholipid (determined by the enzyme method) and beta-lipoprotein (determined by turbidmetry) in the serum was observed.

The results are shown in Table 12. In Table 12, the values of serum cholesterol (mean value of 550 mg/dl), of phospholipid (mean value of 320 mg/dl) and of beta-lipoprotein (mean value of 2500 mg/kg) before administration were respectively subtracted from the respective values after 3 and 6 hours of the administration, and only the differences are shown, respectively. Therefore, the minus value shows the decrease and the plus value shows the increase of the respective values due to the administration. As is clearly seen in Table 12, sodium p-aminobenzoate-N-L-rhamnoside exhibited the activity of reducing the lipid components as compared to control.

TABLE 12

| | Activity of reducing blood lipids | | | | | | |
|---|---|---|---|---|---|---|---|
| | Dose | Phospholipid (mg/dl) | | beta-Lipoprotein (mg/dl) | | Cholesterol (mg/dl) | |
| | (mg/kg) | 3 hrs. | 6 hrs. | 3 hrs. | 6 hrs. | 3 hrs. | 6 hrs. |
| Sodium p-aminobenzoate-N—L-rhamnoside | 30 | −49 | −47 | −134 | −161 | −50 | −45 |
| | 300 | −57 | −51 | −24 | −232 | −75 | −70 |
| Control | | 0 | −19 | 0 | +3 | +8 | −4 |

EXAMPLE 8

(Clinical Case 1)

Lung cancer (Squamous epithelial carcinoma) Man of 51: Body weight 60 kg.

On the chest roentgenographycal examination due to the general feeling of malaise and remarkable coughs, he was diagnosed to be unexcisable lung cancer. Internal (oral) administration of 600 mg/day of sodium p-aminobenzoate-N-L-rhamnoside was begun with an ionizing irradiation. With the continuous administration of sodium p-aminobenzoate-N-L-rhamnoside at 300 mg/day, the subjective symptoms such as pain in chest, etc. disappeared with the improved appetite and the general conditions, moreover, with the reduction of the shadow of the tumour at roentgenography. The treatment with the present substance (sodium p-aminobenzoate-N-L-rhamnoside) was judged to be effective.

EXAMPLE 9

(Clinical Case 2)

Stomach cancer (Adenocarcinoma) Man of 62 in age: Body weight 53 kg.

It was an unoperable stomach cancer and just after the laparotomy an intravenous injection of MMC was performed and the incision was closed. After two weeks of the beginning of the internal (oral) administration of sodium p-aminobenzoate-N-L-rhamnoside at 600 mg/day, the reduction of ascites and the improvement of apetite were observed with the improvement of general status. The tumour showed reduction from after one month, and the ascites disappeared in the third month with the reduced tumour (50% of the original size). He was judged to be improved by the standard of cancer therapy.

EXAMPLE 10

(Clinical Case 3)

Esophageal cancer (Squamous epithelial carcinoma) Man of 72: 51 kg.

Examined claiming the dysphagia and a shadow was found in the lower esophagus by roentgenography, he was diagnosed esophageal cancer by endoscopy. No improvement was observed after an ionizing irradiation and the internal (oral) administration of sodium-p-aminobenzoate-N-L-rhamnoside of 300 mg/day was begun. After about 4 months, improvements were observed in roentgenography and endoscopy and biopsy did not find any malignant images. Now, after 2 years, he is still under treatments, however, the course is favorable without any recurrence.

EXAMPLE 11

(Clinical Case 4)

Malignant lymphoma (Lymphosarcoma) Woman of 47: Body weight 48 kg.

She had lymphosarcoma of Stage IV with primary lesion at the neck and the axilla. Treatment of remission was introduced by ionic irradiation and DAMP. Metastases were observed in the inguinal region and the lungs. On the continued internal (oral) administration of 300 mg/day of the sodium p-aminobenzoate-N-L-rhamnoside, the swelling of cervical lymph node and of axillal lymphnode showed a gradual reduction not to be palpable. Now, after one and a half year, she is in the stage of remaining remission and judged as 1-C by the Kalnofsky's criteria

EXAMPLE 12

(Clinical Case 5)

Recurrent uterine cervical cancer (Squamous epitherial cancer) Woman of age of 55: Body weight 46 kg.

Hospitalized under the diagnosis of uterine cervical cancer of Stage III, and once dehospitalized on the improvement due to an external irradiation from $^{60}$Co, and to an intravaginal irradiation from $^{137}$Cs. After that, on the topical recurrence of the tumour, the ionic irradiation was not effective and the internal (oral) administration of sodium p-aminobenzoate-N-L-rhamnoside was begun at 300 mg/day. Although at that time the body weight loss, the general feeling of malaise and the loss of apetite were remarkable, after about one month, the course of the general conditions became favorable including improved apetite with the recovery of the body weight, however, without any sign of recurrence or metastasis.

What is claimed is:

1. A method of inhibiting tumor growth in a patient suffering therefrom, which comprises administering to said patient a pharmaceutically effective amount of p-aminobenzoate-N-L-rhamnoside or a pharmaceutically acceptable salt thereof.

2. A method of claim 1 wherein the active ingredient is said pharmaceutically acceptable salt which is the sodium salt.

3. A method of claim 2 via oral administration wherein said pharmaceutically effective amount per day is from about 1 to 500 mg per kg.

4. A method of claim 2 via parenteral administration wherein said pharmaceutically effective amount per day is from about 0.01 to about 200 mg per kg.

5. The method of claim 1 wherein said tumor is squamous epithelial carcinoma.

6. The method of claim 1 wherein said tumor is adenocarcinoma.

7. The method of claim 1 wherein said tumor is lymphosarcoma.

8. A method for the treatment of tumor, which comprises administering to a patient suffering therefrom a pharmaceutically effective amount of p-aminobenzoate-N-L-rhamnoside or a pharmaceutically acceptable salt thereof.

9. A method of claim 8 wherein the active ingredient is said pharmaceutically acceptable salt which is the sodium salt.

10. A method of claim 9 via oral administration wherein said pharmaceutically effective amount per day is from about 1 to 500 mg per kg.

11. A method of claim 9 via parenteral administration wherein said pharmaceutically effective amount per day is from about 0.01 to about 200 mg per kg.

12. The method of claim 8 wherein said tumor is squamous epithelial carcinoma.

13. The method of claim 8 wherein said tumor is adenocarcinoma.

14. The method of claim 8 wherein said tumor is lymphosarcoma

* * * * *

UNITED STATES PATENT AND TRADEMARK OFFICE
CERTIFICATE OF CORRECTION

PATENT NO. : 4,748,159
DATED : May 31, 1988
INVENTOR(S) : Chikao Yoshikumi et al It is certified that error appears in the above-identified patent and that said Letters Patent is hereby corrected as shown below:

On the title page, Foreign Application Data Item (30) "Dec. 29, 1979" should read -- Dec. 29, 1978 --.

Signed and Sealed this

Seventeenth Day of January, 1989

Attest:

DONALD J. QUIGG

*Attesting Officer*    Commissioner of Patents and Trademarks